(12) United States Patent
Xu

(10) Patent No.: US 9,845,315 B2
(45) Date of Patent: Dec. 19, 2017

(54) METHOD FOR PREPARING AFATINIB AND INTERMEDIATE THEREOF

(71) Applicants: SUZHOU MIRACPHARMA TECHNOLOGY CO., LTD., Suzhou (CN); Xuenong Xu, Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 14/957,607

(22) Filed: Dec. 3, 2015

(65) Prior Publication Data

US 2016/0083373 A1 Mar. 24, 2016

Related U.S. Application Data

(63) Continuation of application No. 14/935,454, filed on Nov. 9, 2015, now abandoned, and a continuation of application No. PCT/CN2014/076536, filed on Apr. 30, 2014.

(30) Foreign Application Priority Data

May 10, 2013 (CN) .......................... 2013 1 0173417
May 10, 2013 (CN) .......................... 2013 1 0173504
May 10, 2013 (CN) .......................... 2013 1 0173691

(51) Int. Cl.
   *C07D 405/12* (2006.01)
   *C07D 307/20* (2006.01)

(52) U.S. Cl.
   CPC ......... *C07D 405/12* (2013.01); *C07D 307/20* (2013.01)

(58) Field of Classification Search
   None
   See application file for complete search history.

*Primary Examiner* — Noble E Jarrell
(74) *Attorney, Agent, or Firm* — Perkins Coie LLP

(57) ABSTRACT

Revealed in the present invention is a method for preparing Afatinib (I): using 2-nitrile-4-[4-(N,N-dimethylamino-1-oxo-2-buten-l-yl]amino-5-[(S)-(tetrahydrofuran-3-yl)oxy] aniline (II) and 4-fluoro-3-chloroaniline (III) as starting materials, and respectively performing a condensation and cyclization reaction with N,N-dimethylformamide dimethylacetal (IV) to prepare Afatinib (I), wherein the method significantly reduces the manufacturing steps of Afatinib and greatly lower the costs. In addition, also provided in the present invention is a method for preparing an intermediate of Afatinib, wherein the method has a stable process, uses readily available starting materials, has a low cost, and all the reactions are classic reactions, suitable for meeting amplification requirements in the industry.

8 Claims, No Drawings

METHOD FOR PREPARING AFATINIB AND INTERMEDIATE THEREOF

CROSS REFERENCE TO RELATED APPLICATIONS

This application is a continuation of U.S. Ser. No. 14/935,454 filed Nov. 9, 2015, which is a continuation of PCT/CN2014/076536 filed Apr. 30, 2014, which claims priority to CN 201310173504.9 filed May 10, 2013, CN 201310173417.3 filed May 10, 2013 and CN 201310173691.0 filed May 10, 2013, all of which are incorporated herein by reference.

TECHNICAL FIELD

The present invention relates to the technical field of organic synthesis route design and preparation of API and intermediates, in particular, to the method for preparing Afatinib and its intermediate.

BACKGROUND ART

Afatinib is a multi-target small molecule drug researched and developed by German Boehringer Ingelheim. It is an irreversible inhibitor of epidermal growth factor receptor (EGFR) and human epidermal receptor (HER2) tyrosine kinase, and also the first drug for lung cancer when failure by the treatment of EGFR inhibitor. Clinically Afatinib can be used for treatment of advanced non-small cell lung cancer and advanced breast cancer, and intestinal cancer. This drug was approved to appear on the markets by US FDA and European EMEA on Jul. 12, 2013 and Sep. 25, 2013 respectively through US FDA Fast Track, which is applicable for first-line treatment of the advanced non-small cell lung cancer (NSCLC) and HER2-positive advanced breast cancer patients. Its trade names are Gilotrif (United States) and Giotrif (EU) respectively.

The chemical name of Afatinib (I) is 4-[(3-chloro-4-fluorophenyl) amino]-6-{[4-(N,N-dimethylamino)-1-oxo-2-buten-1-yl] amino}-7-[(S)-(tetrahydrofuran-3-yl) oxy] quinazoline.

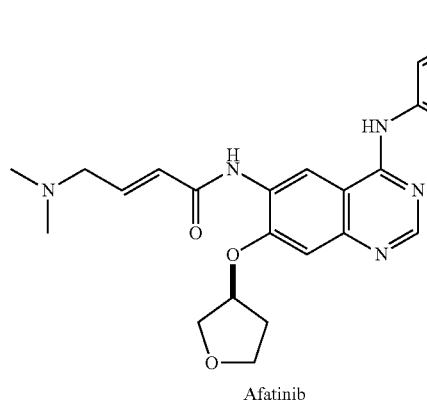

Afatinib

The global patent No. WO0250043A1 and No. WO03094921A2 for original research of Boehringer Ingelheim reported the preparation method of Afatinib: using parent nucleus 4-[(3-chloro-4-fluorophenyl) amino]-6-nitro-7-fluoro-quinazoline (XII) as a starting material, substitution reaction with S-3-hydroxy-tetrahydrofuran occurs under the catalyzation of potassium tert-butoxide, to produce 4-[(3-chloro-4-fluorophenyl) amino]-6-nitro-7-[(S)-(tetrahydrofuran-3-yl) oxy] quinazoline (XIII); after 6-position nitro-reduction, get the corresponding amide (XIV) which reacts with bromo-crotonyl chloride to get the intermediate (XV) through amidation reaction. After amination reaction between intermediate (XV) and dimethylamine, get Afatinib (I).

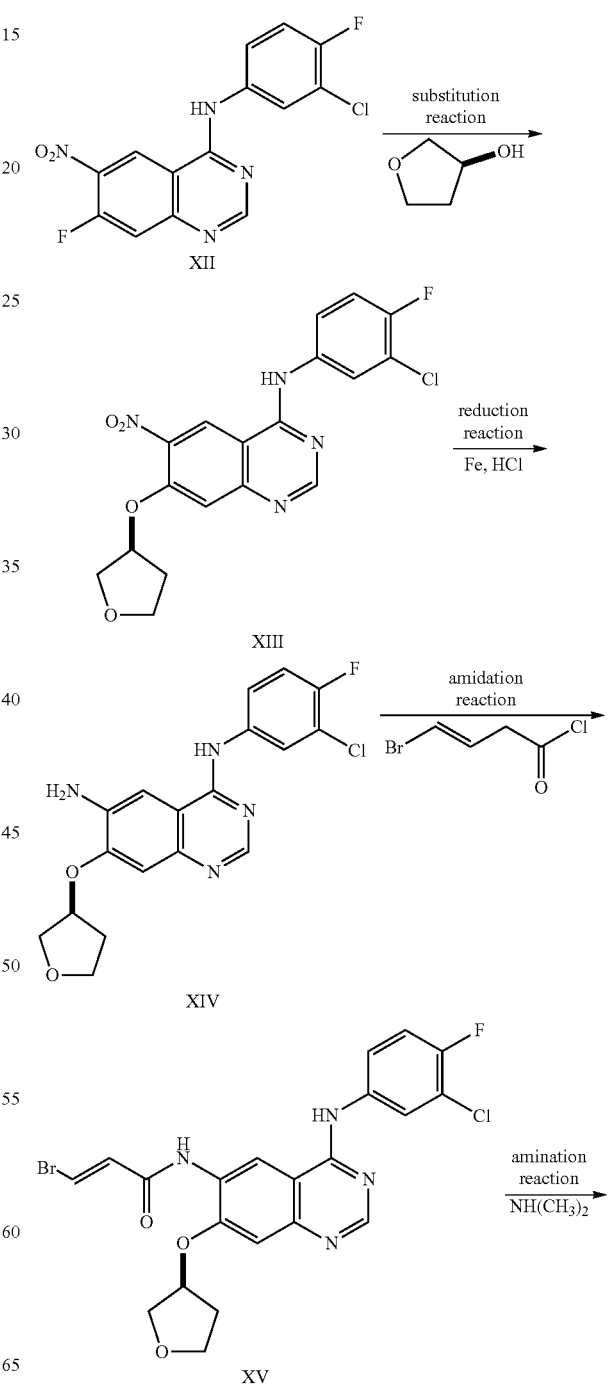

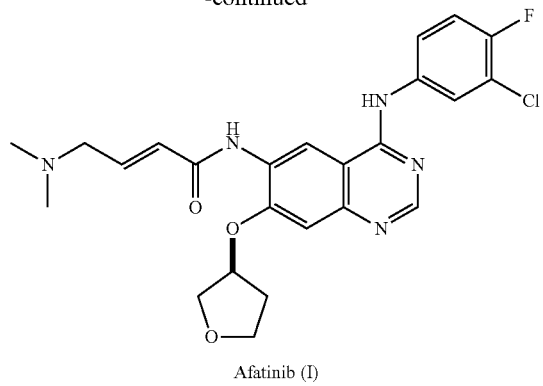

Afatinib (I)

This shows that the key of Afatinib preparation technology is the structural design of quinazoline nucleus and the selection of cyclization time. Currently, the preparation method of Afatinib is to modify the functional group at 7- and 6-position sequentially through 4-position functionalized quinazoline nucleus (XII). This method should firstly prepare the quinazoline nucleus, then transformation of side chain functional group, thus it includes multiple steps, with a low total yield; moreover, column chromatography is necessary used for separation and purification in many steps, thus, it is not applicable for industrialization.

SUMMARY OF THE INVENTION

One of the objects of the present invention is to provide a new method for preparing Afatinib according to the atom economy synthesis concept of green chemistry. The method uses readily available starting materials, with simple process, economy and environmental protection, which can facilitate the industrial production of drug and promote the economic and technological development of the API.

To achieve the above object, the invention provides the main technical solution I as follows: A method for preparing Afatinib (4-[(3-chloro-4-fluorophenyl) amino]-6-{[4-(N,N-dimethylamino)-1-oxo-2-buten-1-yl] amino}-7-[(S)-(tetrahydrofuran-3-yl)oxy] quinazoline, I),

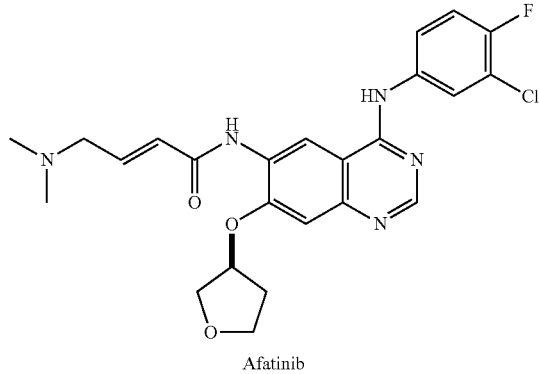

Afatinib comprising the following steps: condensation reaction occur between N,N-dimethylformamide dimethyl acetal (IV) and 2-nitrile-4-[4-(N,N-dimethylamino)-1-oxo-2-buten-1-yl] amino-5-[(S)-(tetrahydrofuran-3-yl)oxy] aniline (II) firstly, to product the intermediate N'-[5-nitrile-4-[4-(N,N-dimethylmethylene)amino]-2-[(S)-(tetrahydrofuran-3-yl) oxy] phenyl]-4-(N,N-dimethylformamide)-2-butenamide (V), and then the intermediate (V) has a cyclization reaction with 4-fluoro-3-chloroaniline (III) directly, to prepare Afatinib (I).

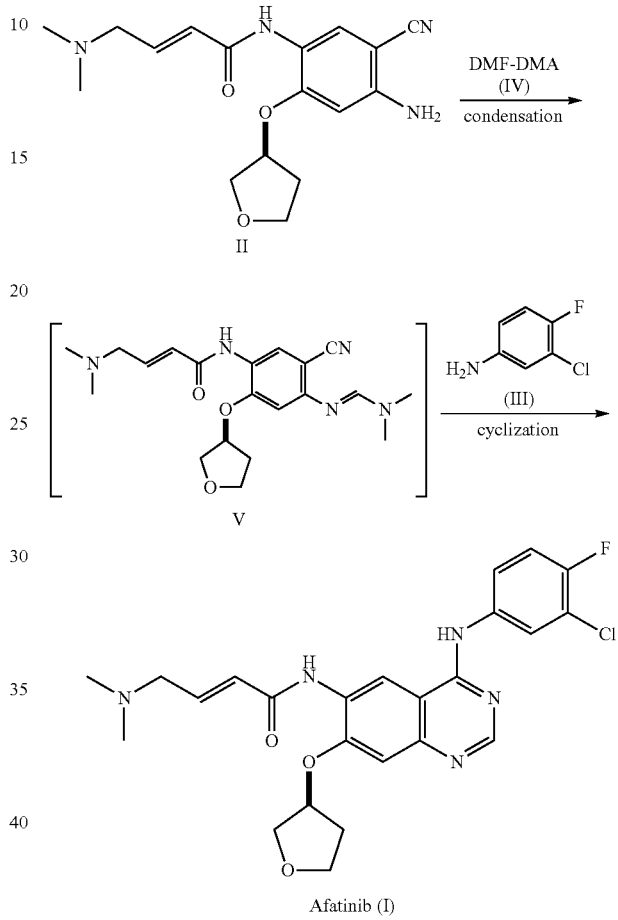

To achieve the above object, the invention provides the main technical solution II as follows: A method for preparing Afatinib (4-[(3-chloro-4-fluorophenyl) amino]-6-{[4-(N,N-dimethylamino)-1-oxo-2-buten-1-yl] amino}-7-[(S)-(tetrahydrofuran-3-yl) oxy] quinazoline, I), comprising the following steps: condensation reaction occur between N,N-dimethylformamide dimethyl acetal (IV) and 4-fluoro-3-chloroaniline (III) firstly, to product the intermediate 4-fluoro-3-chloro-[N'-(N,N-dimethylmethylene)] aniline (VI), then the intermediate (VI) has a cyclization reaction with 2-nitrile-4-[4-(N,N-dimethylamino)-1-oxo-2-buten-1-yl]amino-5-[(S)-(tetrahydrofuran-3-yl)oxy] aniline (II) directly, to prepare Afatinib (I).

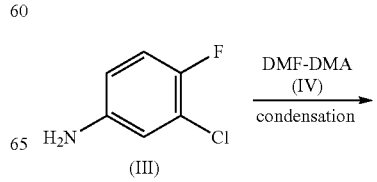

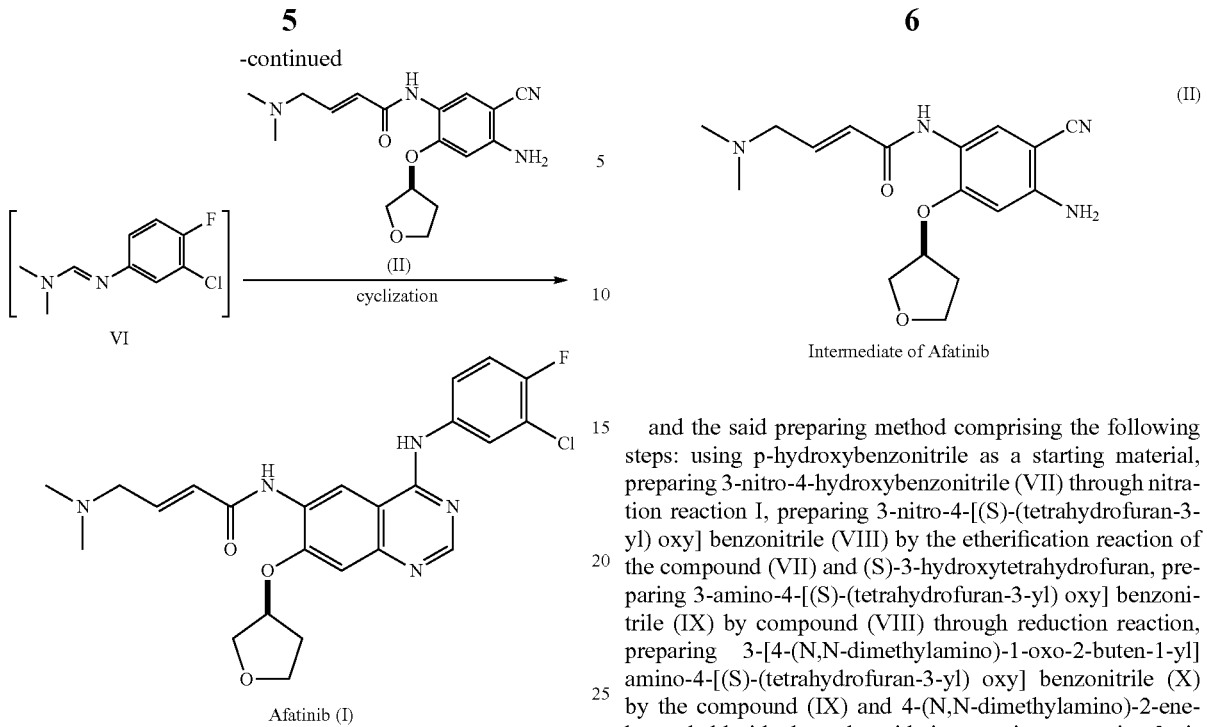

In addition, the invention also provides the following additional technical solutions:

The molar ratio of 2-nitrile-4-[4-(N,N-dimethylamino)-1-oxo-2-buten-1-yl] amino-5-[(S)-(tetrahydrofuran-3-yl) oxy] aniline (II) to N,N-dimethylformamide dimethyl acetal (IV) is 1:1-2, preferably 1:1.3-1.5.

The molar ratio of 4-fluoro-3-chloroaniline (III) to N,N-dimethylformamide dimethyl acetal (IV) is 1:1-2, preferably 1:1.3-1.5.

The catalysts of condensation reaction are formic acid, acetic acid, methanesulfonic acid, sulfuric acid or phosphoric acid, preferably acetic acid.

The temperature of condensation reaction is 0-150° C.

The solvents of condensation reaction are toluene, xylene, dioxane, 1,2-dichloroethane, dimethylsulfoxide, or tetrahydrofuran.

The temperature of cyclization reaction is 0-150° C.

The alkaline neutralizing agents involved in post-treatment of cyclization reaction are sodium hydroxide, potassium hydroxide, sodium bicarbonate, sodium carbonate, sodium methoxide, ammonia or triethylamine.

The solvents of cyclization reaction are formic acid, acetic acid, or a mixture of the two acids formed with toluene respectively, preferably acetic acid or a mixture of acetic acid with toluene.

In addition, another object of the present invention is to provide a new method for preparing intermediate of Afatinib, wherein the method has a stable process, uses readily available starting materials, has a low cost, and all the reactions are classic reactions, suitable for meeting amplification requirements in the industry.

To achieve the above object, the invention provides the technical solution III as follows: A method for preparing an intermediate of Afatinib, wherein the intermediate is 2-nitrile-4-[4-(N,N-dimethylamino)-1-oxo-2-buten-1-yl]amino-5-[(S)-(tetrahydrofuran-3-yl)oxy] aniline (II), and the said preparing method comprising the following steps: using p-hydroxybenzonitrile as a starting material, preparing 3-nitro-4-hydroxybenzonitrile (VII) through nitration reaction I, preparing 3-nitro-4-[(S)-(tetrahydrofuran-3-yl) oxy] benzonitrile (VIII) by the etherification reaction of the compound (VII) and (S)-3-hydroxytetrahydrofuran, preparing 3-amino-4-[(S)-(tetrahydrofuran-3-yl) oxy] benzonitrile (IX) by compound (VIII) through reduction reaction, preparing 3-[4-(N,N-dimethylamino)-1-oxo-2-buten-1-yl] amino-4-[(S)-(tetrahydrofuran-3-yl) oxy] benzonitrile (X) by the compound (IX) and 4-(N,N-dimethylamino)-2-enebutyryl chloride through amidation reaction, preparing 2-nitro-5-[4-(N,N-dimethylamino)-1-oxo-2-buten-1-yl] amino-4-[(S)-(tetrahydrofuran-3-yl) oxy] benzonitrile (XI) by the compound (X) through nitration reaction II, and preparing 2-nitrile-4-[4-(N,N-dimethylamino)-1-oxo-2-buten-1-yl] amino-5-[(S)-(tetrahydrofuran-3-yl) oxy] aniline (II) by the compound (XI) through reduction reaction.

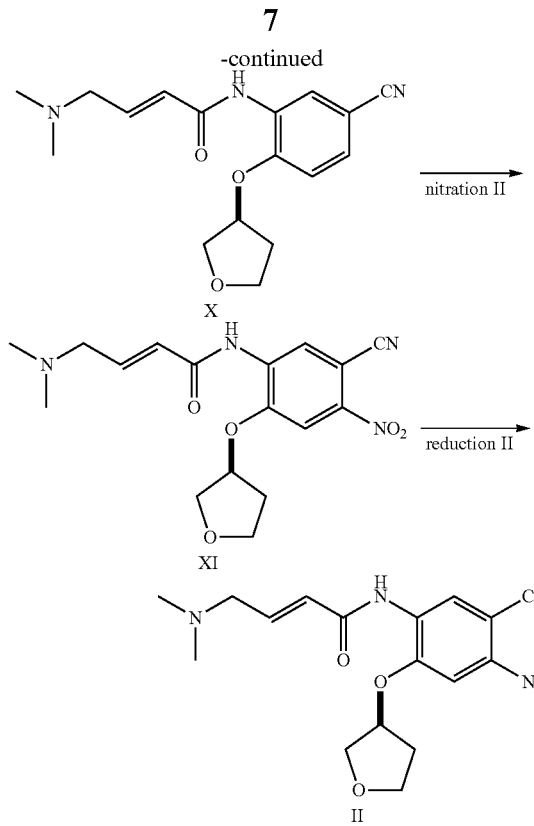

In addition, the preparation of the intermediate of Afatinib also includes the following additional technical solutions:

The raw materials of said etherification reaction are 3-nitro-4-hydroxybenzonitrile (VII) and (S)-3-hydroxytetrahydrofuran, with a molar ratio of 1:1-3, preferably 1:1.5-2.5.

The accelerants of etherification reaction are dimethyl azodicarboxylate (DEAD), diisopropyl azodiformate (DIAD), dipropyl azodicarboxylate (DPAD), dimethyl azodicarboxylate (DMAD), 2-p-chlorobenzyl chloride azodicarboxylate (DCAD), N,N,N',N'-tetramethylazodicarboxamide dicarboxamide (TMAD), N,N,N',N'-tetraisopropyl azobis-carboxamide (TIPA) or azodicarbonyl dipiperidine (ADDP), preferably dimethyl azodicarboxylate (DEAD) or diisopropyl azodiformate (DIAD).

The accelerants of etherification reaction are triphenylphosphine (TPP), tributylphosphine (TBP), trimethylphosphine (TMA) or cyanomethylenetributylphosphorane (CMBP), preferably triphenylphosphine (TPP) or tributylphosphine (TBP).

The solvents of etherification reaction are toluene, xylene, ethyl acetate, isopropyl acetate, butyl acetate, dioxane, dichloromethane, chloroform, 1,2-dichloroethane, dimethylsulfoxide, acetonitrile, N,N-dimethylformamide, acetone or tetrahydrofuran, preferably dichloromethane or tetrahydrofuran.

The starting materials of amidation reaction are 3-amino-4-[(S)-(tetrahydrofuran-3-yl) oxy] benzonitrile (IV) and 4-(N,N-dimethylamino)-2-ene-butyryl chloride, with a molar ratio of 1:1-2, preferably 1:1.1-1.3.

The acid-binding agents of amidation reaction are triethylamine, pyridine, N-methyl morpholine, diisopropylethylamine, sodium hydroxide, sodium methoxide, sodium hydroxide, potassium hydroxide, sodium carbonate, sodium bicarbonate or potassium carbonate, preferably triethylamine or potassium carbonate.

The solvents of said amidation reaction are dichloromethane, chloroform, toluene, acetonitrile, or dimethylsulfoxide, preferably dichloromethane.

The temperature of said amidation reaction is 0-60° C., preferably 20-25° C.

Compared to prior art, the method for preparing Afatinib herein has the following advantages: the starting materials are easily available; the process is simple, economical and environmentally-friendly, facilitating the industrial production of the drugs and promoting the economical and technological development of the API. The preparation method of intermediate has a stable process, uses readily available starting materials, has a low cost, and all the reactions are classic reactions, suitable for meeting amplification requirements in the industry.

DETAILED DESCRIPTIONS OF THE PREFERRED EMBODIMENTS

The invention is described herein in connection with several embodiments. Among them, nitration reaction I, reduction reaction I, nitration reaction II and reduction reaction II are the well-known classic reactions. Specifically the nitration reactions can refer to Chemical World (Page 237, Issue 4, Volume 25, 2013) or Tetrahedron Letters (Page 5393, Issue 40, Volume 53, 2012); the reduction reaction can adopt Pd/C hydrogenation system, iron acetate system, hydrazine hydrate ferric chloride system or sodium dithionite (sodium hydrosulfite) system. For side chain (S)-3-hydroxytetrahydrofuran and 4-(N,N-dimethylamino)-2-ene-butyryl chloride, refer to the description of the preparation method of similar compounds in World Patent No. WO0250043A1 and No. WO03094921 A2.

Embodiment I (Technical Solution I)

12.0 g of 2-nitrile-4-[4-(N,N-dimethylamino)-1-oxo-2-buten-1-yl] amino-5-[(S)-(tetrahydrofuran-3-yl) oxy] aniline (II) (0.036 mol), 6.5 g of N,N-dimethylformamide dimethyl acetal (IV) (0.054 mol) and 150 mL toluene were added to a 500 mL three-necked flask, and added with 3.5 mL acetic anhydride as the catalyst under stirring state. The mixture was heated to 105-110° C., maintained at this temperature for reaction 3 hours (methanol was collected by an oil-water separator), then the reaction ended with the TLC monitoring. Toluene was recovered by distillation under the reduced pressure at 50° C., to get 12.8 g of light brown oily substance with the yield of 92.4%, which could be directly used in the following procedures without separation.

The above oily substance was dissolved in 150 mL acetic anhydride, transferred to a 500 mL three-necked flask; then added with 3-chloro-4-fluoroaniline (III) (7.13 g, 0.049 mol) to stir, heated to 115-125° C. and kept at reflux for 6 hours, to end the reaction with the TLC monitoring. The mixture was cooled down to room temperature, and adjusted to pH 8-9 with 5% ammonia to separate out solid substance. The temperature was slowly reduced to 5° C., one hour after stirring and crystallizing, the solution was filtered and the filter cake was washed by ethyl acetate. Recrystallization was performed with methanol, acetone and water successively, and dried under vacuum state at 40-50° C. to get 12.4 g white solid Afatinib (I), with a yield of 77.0%.

Embodiment II (Technical Solution I)

12.0 g of 2-nitrile-4-[4-(N,N-dimethylamino)-1-oxo-2-buten-1-yl] amino-5-[(S)-(tetrahydrofuran-3-yl) oxy] aniline (II) (0.036 mol), 6.5 g of N,N-dimethylformamide dimethyl acetal (IV) (0.054 mol) and 150 mL toluene were added to a 500 mL three-necked flask, and added with 3.4 mL acetic anhydride as the catalyst under stirring state. The mixture was heated to 105-110° C., maintained at this temperature for reaction 3 hours (methanol was collected by an oil-water separator), then the reaction ended with the TLC monitoring. Toluene was recovered by distillation under the reduced pressure at 50° C., to get 12.1 g of light brown oily substance with the yield of 87.3%, which could be directly used in the following procedures without separation.

The above oily substance was dissolved in 25 mL acetic anhydride and 125 mL of toluene, transferred to a 500 mL three-necked flask; then added with 3-chloro-4-fluoroaniline (III) (7.0 g, 0.048 mol) to stir, heated to 120-130° C. and kept at reflux for 4 hours, to end the reaction with the TLC monitoring. The mixture was concentrated to ⅓ volume, cooled down to room temperature, and adjusted to pH 8-9 with 5% ammonia to separate out solid substance. The temperature was slowly reduced to 5° C., one hour after stirring and crystallizing, the solution was filtered and the filter cake was washed by ethyl acetate. Recrystallization was performed with methanol, acetone and water successively, and dried under vacuum state at 40-50° C. to get 11.9 g white solid Afatinib (I), with a yield of 78.0%.

Embodiment III (Technical Solution II)

14.5 g of 3-chloro-4-fluoroaniline (0.10 mol), 17.8 mL of N,N-dimethylformamide dimethyl acetal (IV) (0.14 mol) and 150 mL toluene were added to a 500 mL three-necked flask, and added with 2.8 mL acetic anhydride as the catalyst under stirring state. The mixture was heated to 105-110° C., maintained at this temperature for reaction 3 hours (methanol was collected by an oil-water separator), then the reaction ended with the TLC monitoring. Toluene was recovered by distillation under the reduced pressure at 50° C., to get 19.5 g of colorless oily substance with the yield of 97.4%, which could be directly used in the following procedures without separation.

The above oily substance was dissolved in 150 mL acetic anhydride, transferred to a 500 mL three-necked flask; then added with 2-nitrile-4-[4-(N,N-dimethylamino)-l-oxo-2-buten-l-yl]amino-5-[(S)-(tetrahydrofuran-3-yl)oxy] aniline (II) (23.8 g, 0.072 mol) to stir, heated to 115-120° C. and kept at reflux for 4 hours, to end the reaction with the TLC monitoring. Most of acetic acid was recovered by distillation under reduced pressure state, cooled down to room temperature, and adjusted to pH 8-9 with 5% ammonia to separate out solid substance. The temperature was slowly reduced to 5° C., one hour after stirring and crystallizing, the solution was filtered and the filter cake was washed by ethyl acetate. Recrystallization was performed with methanol, acetone and water successively, and dried under vacuum state at 40-50° C. to get 24.5 g light yellow solid Afatinib, with a yield of 70.2%.

Embodiment IV (Technical Solution II)

14.5 g of 3-chloro-4-fluoroaniline (0.10 mol), 17.8 mL of N,N-dimethylformamide dimethyl acetal (IV) (0.14 mol) and 150 mL toluene were added to a 500 mL three-necked flask, and added with 2.5 mL anhydrous formic acid as the catalyst under stirring state. The mixture was heated to 105-110° C., maintained at this temperature for reaction 4 hours (methanol was collected by an oil-water separator), then the reaction ended with the TLC monitoring. Toluene was recovered by distillation under the reduced pressure at 50° C., to get 19.2 g of colorless oily substance with the yield of 96.2%, which could be directly used in the following procedures without separation.

The above oily substance was dissolved in 25 mL acetic anhydride and 125 mL toluene, transferred to a 500 mL three-necked flask; then added with 2-nitrile-4-[4-(N,N-dimethylamino)-l-oxo-2-buten-l-yl]amino-5-[(S)-(tetrahydrofuran-3-yl)oxy] aniline (II) (22.5 g, 0.068 mol) to stir, heated to 120-130° C. and kept at reflux for 4 hours, to end the reaction with the TLC monitoring. Solvent was recovered by distillation under reduced pressure state, cooled down to room temperature, and adjusted to pH 8-9 with 5% ammonia to separate out solid substance. The temperature was slowly reduced to 5° C., one hour after stirring and crystallizing, the solution was filtered and the filter cake was washed by ethyl acetate. Recrystallization was performed with methanol, acetone and water successively, and dried under vacuum state at 40-50° C. to get 22.9 g off-white solid Afatinib, with a yield of 69.4%.

Embodiment V (Technical Solution III: Preparation of Intermediate II/Nitration Reaction I)

11.9 g of p-Hydroxybenzonitrile (0.1 mol) and 50 mL glacial acetic acid were added to a 250 mL three-necked flask, added dropwise with the mixture of 8 mL concentrated nitric acid and 12 mL glacial acetic acid. After dripping, the solution was slowly heated to 45-50° C. to react 1.5 hours, tested by TLC, the starting materials were reacted completely; then cooled down, added with dichloromethane, standing, to separate the upper organic layer, and then washed by water, 5% sodium bicarbonate solution and saturated brine, 50 mL each. Solvent was recovered under reduced pressure to get 15.5 g of light yellow solid 3-nitro-4-hydroxybenzonitrile (VII), with a yield of 94.5%.

Embodiment VI (Technical Solution III: Preparation of Intermediate II/Etherification Reaction)

3 mL DIAD (15 mmol) and 5 mL tetrahydrofuran were added to a 100 mL three-necked flask under room temperature, and added dropwise with 25 mL of tetrahydrofuran solution of triphenylphosphine (4.0 g, 15 mmol), to react 2 hours at room temperature. With the protection of nitrogen, 5 mL of tetrahydrofuran solution of (S)-3-hydroxytetrahydrofuran (0.3 g, 3.4 mmol) was added dropwise to the above reaction system. After dripping, 0.5 g of 3-nitro-4-hydroxybenzonitrile (VII) (3.0 mmol) was added and stirred for reaction for 4 hours at room temperature, then 5 mL of tetrahydrofuran solution of (S)-3-hydroxytetrahydrofuran (0.23 g, 2.6 mmol) was added dropwise, to continue to react 2 hours at room temperature, and end by TLC monitoring. The solvent was recovered by distillation under reduced pressure and the remnant was adjusted to pH=5-6 with dilute hydrochloric acid, extracted by ethyl acetate. The organic phase was adjusted to pH=10-11 with saturated sodium carbonate, then the aqueous phase was separated out, freeze-dried under vacuum state to get 0.59 g off-white solid 3-nitro-4-[(S)-(tetrahydrofuran-3-yl) oxy] benzonitrile (VIII), with a yield of 83.8%.

Embodiment VII (Technical Solution III: Preparation of Intermediate II/Reduction Reaction I)

2.34 g of 3-nitro-4-[(S)-(tetrahydrofuran-3-yl) oxy] benzonitrile (VIII) (10 mmol), 0.2 g of ferric chloride, 0.4 g of activated carbon and 35 mL of ethanol were added to a 100 mL three-necked flask under room temperature, heated to 50-60° C., then added with 80% hydrazine hydrate (20 mmol, 1.5 mL), kept warm to react 3 hours, detected by TLC until complete reaction. The solution was distilled under reduced pressure to get 1.85 g brown oily substance 3-amino-4-[(S)-(tetrahydrofuran-3-yl) oxy] benzonitrile (IX), with a yield of 90.7%.

Embodiment VIII (Technical Solution III: Preparation of Intermediate II/Amidation Reaction)

3-amino-4-[(S)-(tetrahydrofuran-3-yl) oxy] benzonitrile (IX) (0.51 g, 2.5 mmol), triethylamine (0.25 g, 2.5 mmol) and 20 mL of dichloromethane were added to a 100 mL three-necked flask, heated to 40-45° C., and stirred until the system is dissolved uniformly. When cooled down to below 10° C., 10 mL of dichloromethane solution of 4-(N,N-dimethylamino)-2-ene-butyryl chloride was added dropwise slowly to continue to react 6 hours, and end by TLC monitoring. The reaction solution was washed with 10% sodium bicarbonate solution and water, and dried with anhydrous sodium sulfate. The solvent was recovered under reduced pressure, and the remnant was recrystallized by ethyl acetate to get 0.72 g of white solid 3-[4-(N,N-dimethylamino)-1-oxo-2-buten-1-yl] amino-4-[(S)-(tetrahydrofuran-3-yl) oxy] benzonitrile (X), with a yield of 91.4%.

Embodiment IX (Preparation of Intermediate II/Nitration Reaction II)

3-[4-(N,N-dimethylamino)-1-oxo-2-buten-1-yl] amino-4-[(S)-(tetrahydrofuran-3-yl) oxy] benzonitrile (X) (1.6 g, 5 mmol), potassium nitrate (1.0 g, 10 mmol) and 10 mL of concentrated sulfuric acid (98%) were added to a 50 mL three-necked flask under temperature of 0-5° C., kept below 5° C. to continue to react 0.5 hour while stirring, then warmed to room temperature to react 4 hours, tested by TLC until complete reaction, then added with dichloromethane, standing, to separate the upper organic layer, and then washed by water, 5% sodium bicarbonate solution and saturated brine. Solvent was recovered under reduced pressure and remnant was recrystallized with ethanol and water to get 1.5 g of off-white solid 2-nitro-5-[4-(N,N-dimethylamino)-1-oxo-2-butene-1-yl] amino-4-[(S)-(tetrahydrofuran-3-yl) oxy] benzonitrile (XI), with a yield of 83.3%.

Embodiment X (Preparation of Intermediate II/Reduction Reaction II)

3.6 g of 2-nitro-5-[4-(N,N-dimethylamino)-1-oxo-2-buten-1-yl] amino-4-[(S)-(tetrahydrofuran-3-yl) oxy] benzonitrile (XI) (10 mmol), 0.36 g of 5% palladium on carbon (10% w/w) and 50 mL ethanol were added to a hydrogenation reaction cauldron, holding a pressure of 3-4 kg at room temperature and reacting about 12 hours. The palladium-carbon catalyst was filtered and recovered and the ethyl alcohol was recovered at a reduced pressure. The remnant was recrystallized with ethyl acetate to get 3.1 g white solid 2-nitrile-4-[4-(N,N-dimethylamino)-1-oxo-2-buten-1-yl] amino-5-[(S)-(tetrahydrofuran-3-yl) oxy]aniline (II), with a yield of 94.0%.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A method for preparing Afatinib (4-[(3-chloro-4-fluorophenyl) amino]-6-{[4-(N,N-dimethylamino)-1-oxo-2-buten-1-yl] amino}-7-[(S)-(tetrahydrofuran-3-yl)oxy] quinazoline, I),

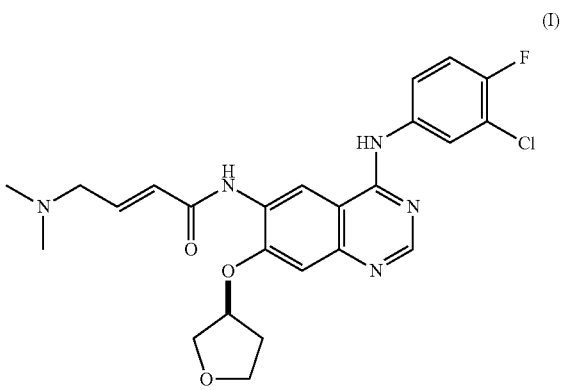

comprising the following steps:
1) a condensation reaction of N,N-dimethylformamide dimethyl acetal (IV) and 2-nitrile-4-[4-(N,N-dimethylamino)-1-oxo-2-buten-1-yl] amino-5-[(S)-(tetrahydrofuran-3-yl)oxy] aniline (II) to product an intermediate N'-[5-nitrile-4-[4-(N,N-dimethylmethylene)amino]-2-[(S)-(tetrahydrofuran-3-yl) oxy] phenyl]-4-(N,N-dimethylformamide)-2-butenamide (V); and
2) a cyclization reaction of the intermediate (V) and 4-fluoro-3-chloroaniline (III) to prepare Afatinib (I).

2. The method for preparing Afatinib according to claim 1, wherein a molar ratio of 2-nitrile-4-[4-(N,N-dimethylamino)-1-oxo-2-buten-l-yl] amino-5-[(S)-(tetrahydrofuran-3-yl)oxy] aniline (II) to N,N-dimethylformamide dimethyl acetal (IV) is 1:1-2.

3. The method for preparing Afatinib according to claim 1, wherein the condensation reaction comprises reacting N,N-dimethylformamide dimethyl acetal (IV) and 2-nitrile-4-[4-(N,N-dimethylamino)-1-oxo-2-buten-l-yl] amino-5-[(S)-(tetrahydrofuran-3-yl)oxy] aniline (II) in the presence of a catalyst selected from the group consisting of formic acid, acetic acid, methanesulfonic acid, sulfuric acid, and phosphoric acid.

4. The method for preparing Afatinib according to claim 1, wherein the condensation reaction comprises reacting N,N-dimethylformamide dimethyl acetal (IV) and 2-nitrile-4-[4-(N,N-dimethylamino)-1-oxo-2-buten-l-yl] amino-5-[(S)-(tetrahydrofuran-3-yl)oxy] aniline (II) at a temperature of 0-150° C.

5. The method for preparing Afatinib according to claim 1, wherein the condensation reaction comprises reacting N,N-dimethylformamide dimethyl acetal (IV) and 2-nitrile-4-[4-(N,N-dimethylamino)-1-oxo-2-buten-l-yl] amino-5-[(S)-(tetrahydrofuran-3-yl)oxy] aniline (II) in a solvent selected from the group consisting of toluene, xylene, dioxane, 1,2-dichloroethane, dimethylsulfoxide, and tetrahydrofuran.

6. The method for preparing Afatinib according to claim 1, wherein the cyclization reaction comprises reacting the intermediate (V) and 4-fluoro-3-chloroaniline (III) in a solvent selected from the group consisting of formic acid, acetic acid, a mixture of formic acid and toluene, and a mixture of acetic acid with toluene.

7. The method for preparing Afatinib according to claim 1, wherein the cyclization reaction comprises reacting the intermediate (V) and 4-fluoro-3-chloroaniline (III) at a temperature of 0-150° C.

8. The method for preparing Afatinib according to claim 1, wherein the cyclization reaction comprises using an alkaline neutralizing agent selected from the group consisting of sodium hydroxide, potassium hydroxide, sodium bicarbonate, sodium carbonate, sodium methoxide, ammonia, and triethylamine.

* * * * *